(12) United States Patent
Sirkar et al.

(10) Patent No.: US 8,036,738 B2
(45) Date of Patent: Oct. 11, 2011

(54) IONTOPHORETIC TRANSDERMAL DRUG DELIVERY SYSTEM BASED ON CONDUCTIVE POLYANILINE MEMBRANE

(75) Inventors: Kamalesh K. Sirkar, Bridgewater, NJ (US); Qiuxi Fan, Allentown, PA (US)

(73) Assignee: New Jersey Institute of Technology, Newark, NJ (US)

( * ) Notice: Subject to any disclaimer, the term of this patent is extended or adjusted under 35 U.S.C. 154(b) by 3 days.

(21) Appl. No.: 11/717,420

(22) Filed: Mar. 13, 2007

(65) Prior Publication Data
US 2007/0232985 A1  Oct. 4, 2007

Related U.S. Application Data

(60) Provisional application No. 60/782,047, filed on Mar. 14, 2006.

(51) Int. Cl.
*A61N 1/30* (2006.01)
(52) U.S. Cl. .................. 604/20; 604/890.1; 604/501
(58) Field of Classification Search .............. 604/20, 604/501, 890.1
See application file for complete search history.

(56) References Cited

U.S. PATENT DOCUMENTS

| | | | |
|---|---|---|---|
| 3,991,755 A | 11/1976 | Vernon et al. | |
| 3,993,072 A | 11/1976 | Zaffaroni | |
| 3,993,073 A | 11/1976 | Zaffaroni | |
| 4,031,894 A | 6/1977 | Urquhart | |
| 4,141,359 A | 2/1979 | Jacobsen et al. | |
| 4,262,003 A | 4/1981 | Urquhart | |
| 4,585,652 A | 4/1986 | Miller et al. | |
| 4,722,726 A | 2/1988 | Sanderson et al. | |
| 4,731,049 A | 3/1988 | Parsi | |
| 4,927,408 A | 5/1990 | Haak et al. | |
| 5,057,072 A | 10/1991 | Phipps | |
| 5,084,008 A | 1/1992 | Phipps | |
| 5,096,586 A | 3/1992 | Kaner et al. | |
| 5,125,894 A * | 6/1992 | Phipps et al. | 604/20 |
| 5,135,477 A | 8/1992 | Untereker et al. | |
| 5,484,884 A | 1/1996 | MacDiarmid et al. | |
| 6,004,309 A * | 12/1999 | Phipps | 604/501 |
| 6,049,733 A * | 4/2000 | Phipps et al. | 604/20 |
| 6,195,582 B1 | 2/2001 | Scott | |
| 6,273,875 B1 | 8/2001 | Siman et al. | |
| 6,330,471 B1 * | 12/2001 | Higo et al. | 604/20 |
| 2002/0022826 A1 | 2/2002 | Reynolds et al. | |
| 2004/0176737 A1 * | 9/2004 | Henley et al. | 604/501 |
| 2004/0193089 A1 | 9/2004 | Fischer et al. | |

(Continued)

OTHER PUBLICATIONS

Q. Fan, K. K. Sirkar, Y. Wang, B. Michniak, *In vitro delivery of doxycycline hydrochloride based on a porous membrane-based aqueous-organic partitioning system*, J. Controlled Release, 98 (3) (2004) 355-365.

(Continued)

*Primary Examiner* — Theodore Stigell
*Assistant Examiner* — Brandy C Scott
(74) *Attorney, Agent, or Firm* — McCarter & English, LLP

(57) ABSTRACT

An iontophoretic transdermal drug delivery system that utilizes a porous conductive polyaniline membrane as one of two electrodes, with both electrodes in contact with an aqueous solution of the ingredient in ionic and nonionic form, and the membrane additionally in contact with the skin surface of the mammal. Upon providing the appropriate direct current flow by voltage generating means through the electrodes and solution, the ingredient is caused to pass through the porous membrane and be released in ionic form through the skin surface of the mammal.

16 Claims, 7 Drawing Sheets

The iontophoretic setup using PANi film as an electrode, the anode (modified from drawings from http://www.permegear.com/o-ring.htm, last accessed on July 3, 2005).

U.S. PATENT DOCUMENTS

2004/0248320 A1* 12/2004 Santini et al. .................. 436/174
2005/0266568 A1* 12/2005 Fujihara et al. ............... 435/459
2007/0255195 A1* 11/2007 Adachi ........................... 604/20

OTHER PUBLICATIONS

Q. Fan, *In Vitro Drug Delivery Based on Porous Membrane-Based Aqueous-Organic Partitioning System and It's Enhancements Through Mouse Skin*, A Dissertation Submitted to the Faculty of New Jersey Institute of Technology in Partial Fulfillment of the Requirement for the Degree of Doctor of Philosophy, (Jan. 2005) 1-93.

Zhou Qin-Xin, *Ion Delivery From Conducting Polymer-Polypyrrole*, A Thesis Submitted to the Faculty of the Graduate School of the University of Minnesota in Partial Fulfillment of the Requirements for the Degree of Doctor of Philosophy in Chemistry, (Jul. 5, 1987) 1-194.

Chang, An-Cheng, *Characterization and Properties of Oligomers of 3-Methoxythiophene*, A Thesis Submitted to the Faculty of the Graduate School of the University of Minnesota in Partial Fulfillment of the Requirements for the Degree of Doctor of Philosophy, (Jul. 1987), 1-211.

C. R. Wilke, et al., *Correlation of Diffusion Coefficients in Dilute Solutions*, AIChE J. I (1955) 264-270.

Kratohvil, et al., *The Influence of the Composition and the Properties of the Solvent on Complex Formation Between Silver and Chloride, Bromide, Iodide, and Thiocyanate Ions*, Recueil des Travaux Chimiques des Pays-Bas et de la Belgique, 75 (1956) 774-780.

P. Anderson, et al., *The Solubility of Silver Chloride and the Concentration of Silver-Containing Species in Ethanol-Water Mixtures*, J. Physical Chemistry, 71 (11) (1967) 3566-3569.

J. S. Newman, *Electrochemiical Systems*, Prentice-Hall, Englewood Cliffs, New Jersey, pp. 227, Table 75-1,1973.

J. B. Bogardus, et al.., *Solubility of Doxycycline in Aqueous Solution*, J. Pharm. Sci. 68 (1979) 188-194.

R. Prasad, et al., *Dispersion-Free Solvent Extraction With Microporous Hollow-Fiber Modules*, AIChE. J. 44 (1988) 177-188.

J. B. Phipps, et al., *Iontophoretic Delivery of Model Inorganic and Drug Ions*, J. of Pharm. Sci. 78(5) (1989) 365-369.

K. A. Walters, et al., *Penetration Enhancers and Their Use in Transdermal Therapeutic Systems*, Transdermal Drug Delivery, Developmental Issues and Research Initiatives, Marcel Dekker, Inc., New York, 1989, Chapter 10.

MMWR, Recommendations and Reports, *Recommendations for the Prevention of Malaria Among Travelers, Morbidity and Mortality Weekly Report*, 39 (RR-3) (1990) 1-10.

M. J. Pikal, *The Role of Electroosmotic Flow in Transdermal Iontophoresis*, Advanced Drug Delivery Reviews, 9 (2-3) (1992) 201-237.

P. Singh, H. et al., *Iontophoresis in Drug Delivery: Basic Principles and Applications*, Critical Reviews in Therapeutic Drug Carrier Systems, II (2&3) (1994) 161-213.

H. Sjöberg, et al., *Ionization Conditions for Iontophoretic Drug Delivery. A Revised Pka of Lidocaine Hydrochloride in Aqueous Solution At 25° C. Established by Precision Conductometry*, Int. J Pharm. 141 (1996) 63-70.

S. Farrell, *A Controlled Release Technique Using Microporous Membranes*, Ph. D. Dissertation, New Jersey Institute of Technology, 1996.

J. E. Riviere, et al.t, *Electrically-Assisted Transdermal Drug Delivery*, Pharm. Research, 14 (6) (1997) 687-697.

K. Kararni, et al., *Ionization Conditions for Iontophoretic Drug Delivery. Electrical Conductance and Aggregation of Lidocaine Hydrochloride in 1-Octanol At 25° C.*, Int. J Pharm. 154 (1997) 79-87.

S. Farrell, et al., *A Reservoir-Type Controlled Release Device Using Aqueous-Organic Partitioning and a Porous Membrane*, J. Membr. Sci. 130 (1997) 265-274.

K. Banga, *Iontophoretic Transdermal Drug Delivery* in Electrically Assisted Transdermal and Topical Drug Delivery (Chapter 2), Taylor & Francis Inc., London, UK, 1998, Chapter 2.

M. Cheryan, *Ultrafiltration and Microfiltration Handbook*, CRC Press, Boca Raton, FL, 1998.

H. Chen, et al., *Selective C02 Separation From C02-N2 Mixtures by Immobilized Carbonate-Glycerol Membranes*, Industrial and Engineering Chemistry Research 38(9) (1999) 3489-3498.

L. Wen, et al., *Doping-dependent ion selectivity of polyaniline membranes*, Syn. Metals, 106 (1999) 19-27.

S. Farrell, et al., *A Mathematical Model of an Aqueous-Organic Partition-Based Controlled Release System Using Microporous Membranes*, J. Controlled Rel. 61 (1999) 345-360.

R. Panchagnula, et al., *Transdermal Iontophoresis Revisited*, Current Opinion in Chemical Biology, 4 (2000) 468-473.

D. Marro, et al., *Optimizing Iontophoretic Drug Delivery: Identification and Distribution of the Charge-Carrying Species*, Pharm. Res. 18 (12) (2001) 1709-1713.

G. Illing, et al., *Preparation and Characterization of Polyaniline Based Membrane for Gas Separation*, J. Membrane Sci., 184 (2001) 69-78.

S. B. Kessler, et al., *Definitions*, Membrane Handbook, Chapman and Hall, New York, 1992, Chapter 11; Kluwer Academic, Boston (2001).

S. Farrell, K. et al., *Mathematical Model of a Hybrid Dispersed Network-Membrane-Based Controlled Release System*, J. Controlled Rel. 70 (2001) 51-61.

P. Wang, et al., *Preparation and Characterization of Semi-Conductive Poly(Vinylidene Fluoride)/Polyaniline Blends and Membranes*, Applied Surfaces Sciences, 193 (2002) 36-45.

W. E. Rhodes III, *Iontophoretic Drug Delivery: New Advantages Revitalize an Established Technology*, Drug Delivery Technology, 2 (6) (2002), 34-37.

Mirmohseni, et al., *Preparation and Characterization of Aqueous Polyaniline Battery Using a Modified Polyaniline Electrodes*, Euro. Polym. J., 39 (2003) 219-223.

Y. Wang, et al., *Effects of Fatty Acids and Iontophoresis on the Delivery of Midodrine Hydrochloride and the Structure of Human Skin*, Pharm. Res. 20 (2003) 1612-1618.

C. Williams, et al., *Penetration Enhancers*, Adv. Drug Del. Rev., 56 (2004) 603-618.

Y. N. Kalia, et al., *Iontophoretic Drug Delivery*, Adv. Drug Del. Rev. 56 (2004) 619-658.

A. Luzardo-Alvarez, Iontophoretic Delivery of Ropinirole Hydrochloride: Effect of Current Density and Vehicle Formulation, Pharmaceutical Research, vol. 18, No. 12, Dec. 2001.

Personal communication with Dr. Per Beronius, Sep. 13, 2004.

* cited by examiner

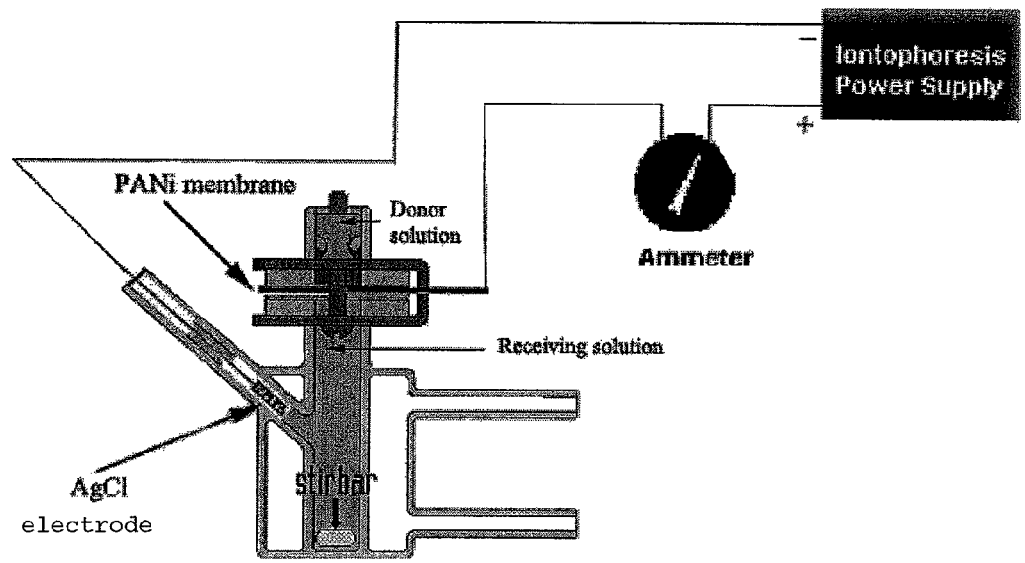
Figure 1. The iontophoretic setup using PANi film as an electrode, the anode (modified from drawings from http://www.permegear.com/o-ring.htm, last accessed on July 3, 2005).

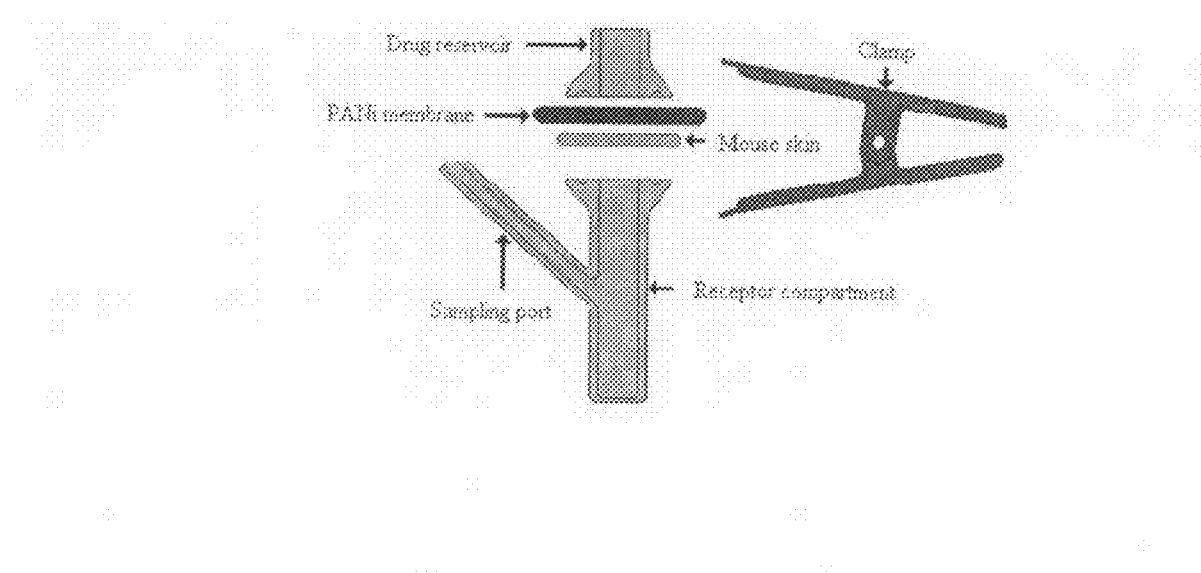
Figure 2. Drug reservoir with PANi and skin membranes (modified from drawings from http://www.permegear.com/o-ring.htm, last accessed on July 3, 2005).

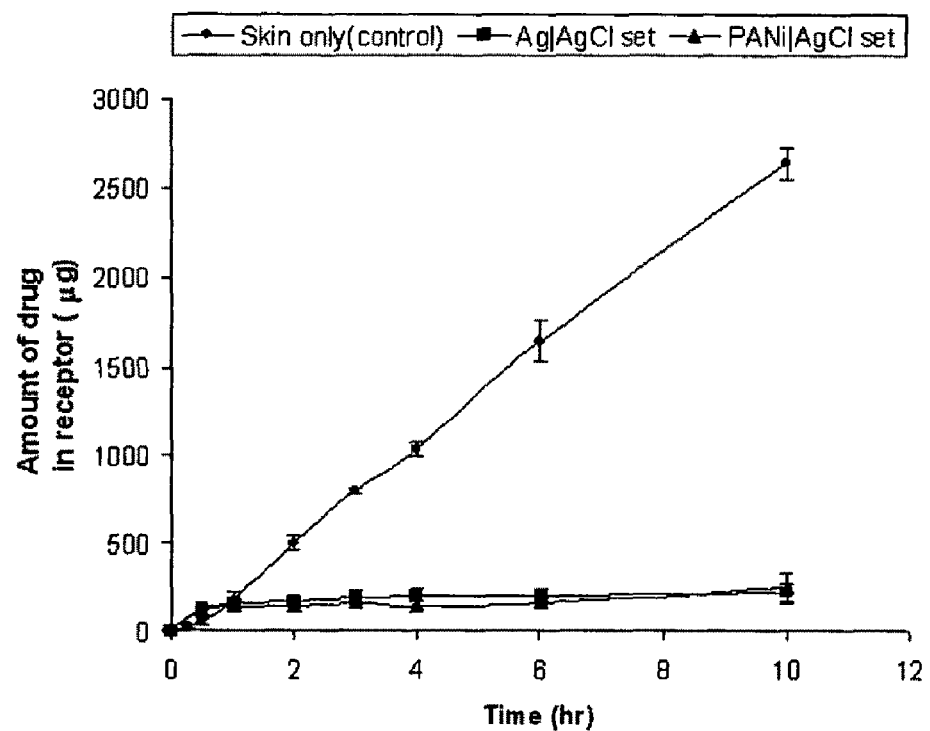
Figure 3. Iontophoretic release profiles of lidocaine HCl through mouse skin with and without a PANi membrane (i=0.2mA/cm$^2$)

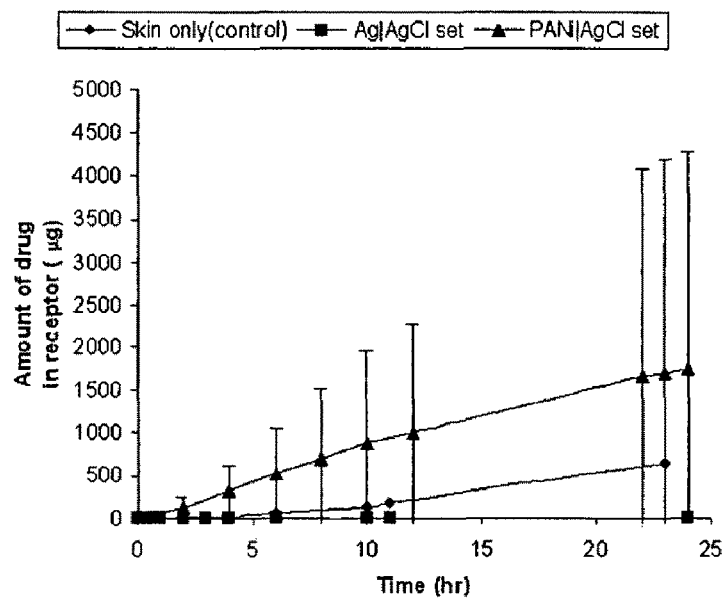
Figure 4. Iontophoretic release profiles of doxycycline HCl through mouse skin with and without a PANi membrane (i=0.3mA/cm$^2$)

Figure 5. SEM picture of doped PANi film used in the Ag|AgCl set for doxycycline HCl diffusion.

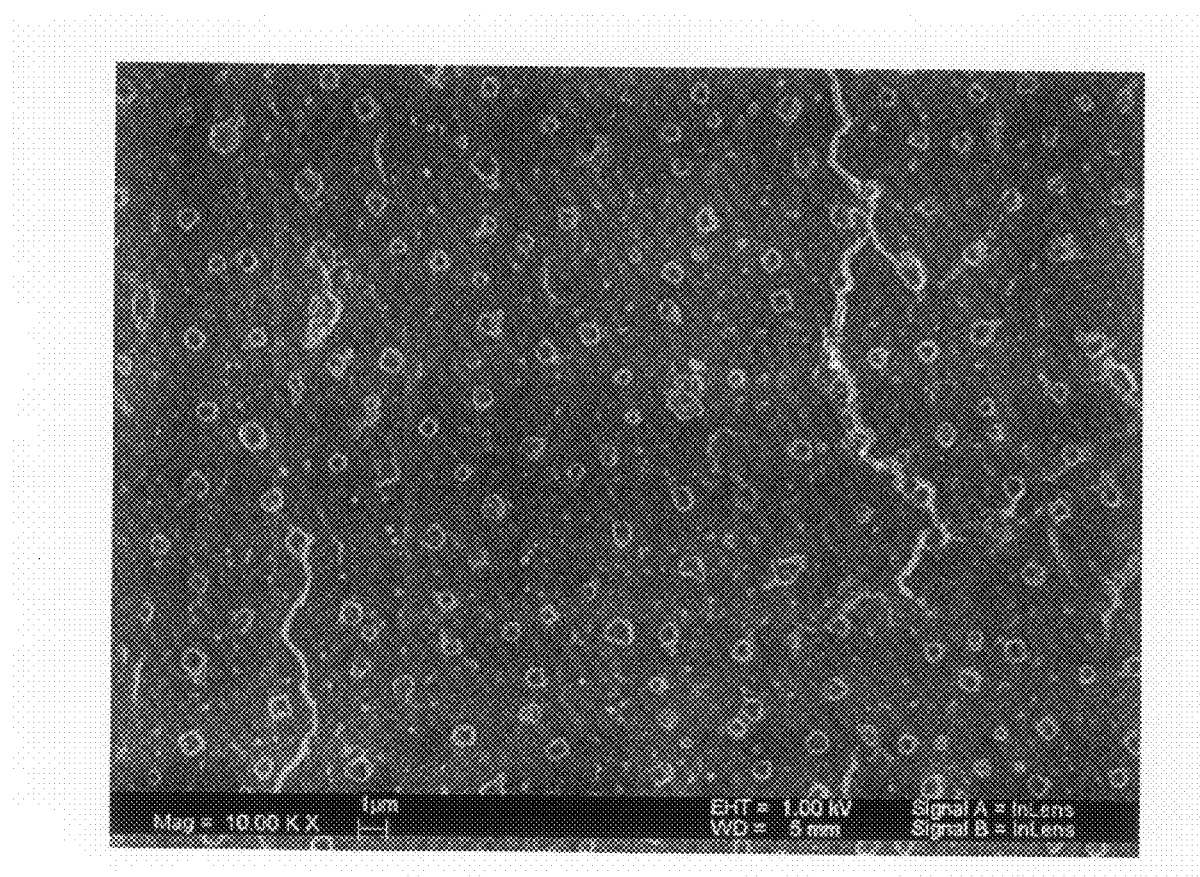
Figure 6. SEM picture of doped PANI film used in the Ag/AgCl set for lidocaine HCl diffusion

Figure 7. SEM picture of doped PANi film used in the PANi|AgCl set for doxycycline HCl diffusion

IONTOPHORETIC TRANSDERMAL DRUG DELIVERY SYSTEM BASED ON CONDUCTIVE POLYANILINE MEMBRANE

CROSS-REFERENCE TO RELATED APPLICATIONS

The present application claims the benefit of a co-pending provisional application entitled "Iontophoretic Transdermal Drug Delivery System Based on Conductive Polyaniline Membrane," which was filed on Mar. 14, 2006 and assigned Ser. No. 60/782,047. The entire contents of the foregoing provisional patent application are incorporated herein by reference.

BACKGROUND

1. Technical Field

The present disclosure is directed to iontophoretic transdermal drug delivery (TDD) systems for pharmaceutically active ingredients and methods of using the same in administration of such ingredients to mammals. More specifically, the TDD system utilizes a porous conductive polyaniline (PANi) membrane as one of two electrodes, with both electrodes in contact with an aqueous solution of the pharmaceutically active ingredient in ionic and nonionic form, and the membrane additionally in contact with the skin surface of the mammal. Upon providing an appropriate direct current flow of electricity by voltage generating means through the electrodes and solution, the pharmaceutically active ingredient is caused to pass through the pores of the membrane and is released in ionic form through the skin surface of the mammal.

2. Background of the Disclosure

While topical drug delivery systems have been used for centuries for the treatment of local skin disorders, the use of the skin as a route for systemic drug delivery is of relatively recent origin. Transdermal administration of drugs has been established in adults in relation to nitroglycerin, estrogens and scopolamine. However, there is a need to develop improved TDD systems which are useful with additional drugs and appropriate for a wider segment of the population.

For a TDD system, the three skin layers of importance are identified as: epidermis, dermis and subcutaneous. The uppermost layer of the epidermis, i.e., the stratum corneum (SC), is the toughest barrier for drug delivery because of its rigid, brick-shaped structure.

Delivery of drugs through a microporous polymeric membrane via aqueous-organic partitioning has been investigated [5-8]. Compared to other conventional controlled release technologies, preparation of such an aqueous-organic partition-based system is convenient and does not require dispersion of the drug into a polymer and the attendant processing steps. Such systems have also been studied in vitro using doxycycline hydrochloride (HCl), a larger (MW: 480.1), polar antibiotic as a model drug with and without mouse skin. In the presence of linoleic acid as a skin transport enhancer, the release rates of this agent were observed to be significant; a simplified mathematical model was developed to successfully describe the experimental data [9].

The prophylactic oral dose of doxycycline is about 700 mg/weekly [10]. If 50% of the drug is bioavailable after the first-pass effect, around 50 mg should be transferred through skin in 24 h. Although the above-noted TDD system using a porous polyvinylidene fluoride (PVDF) membrane [9] can introduce the total amount required in 24 h using appropriate patch dimensions, much faster delivery may be required for other drugs, e.g., lidocaine hydrochloride. Iontophoresis as a means to achieve faster delivery of drug has been researched by the inventors herein to increase the accumulation of drug using a porous polyaniline conducting polymeric membrane as an electrode.

As a non-invasive transdermal drug delivery (TDD) method [1], iontophoresis applies electrical current to deliver solubilized drugs through the skin to either the underlying tissue (local area) or capillaries and then to the whole circulating system (systemically). A voltage applied between two electrodes immersed in a drug solution causes the drug (in the form of charged ions) to be moved from the donor part into the skin. The positively charged electrode, i.e., the anode, attracts the negatively charged drug ions; the negatively charged electrode, i.e., the cathode, attracts the positively charged ions. Usually Ag/AgCl electrodes are used in such a system [2].

There are several advantages to iontophoretic TDD. First, it is a non-invasive way to deliver drug into the body so that great pain is eliminated without mechanical penetration (such as injections) and disruption of the skin. Another advantage is that drugs can be delivered either locally or systemically without potential systemic side effects. As iontophoretic TDD is controlled by the current, the third advantage is that it can also control the timing of drug delivery in an exact fashion which is especially efficient for particular diseases, e.g., Parkinson's disease. Since the current applied is quite low, there is no reason to worry about infection and tissue trauma. However, there are some limitations for iontophoresis, e.g., only water-soluble drugs of molecular weight (MW) under 10,000 ("10,000 Dalton Rule") are amenable to delivery [3]. In addition, prior art iontophoretic TDD systems have caused in some patients redness, burning and/or itching at the drug administration site. Another concern is the size of the power supply, which ideally should be as small and lightweight as possible. In spite of these limitations, the first pre-filled iontophoretic TDD patch for local anesthesia has been approved by the FDA [4].

Despite efforts to date, a need remains for an effective/reliable transdermal delivery system, particularly for higher molecular weight molecules, e.g., doxycycline hydrochloride (HCl). These and other needs are met by the systems and methods disclosed herein.

SUMMARY OF THE PRESENT DISCLOSURE

According to the present disclosure, iontophoretic techniques are employed using a porous conductive polyaniline membrane which is also the electrode for delivering transdermally important antibiotics and other large molecules, e.g., doxycycline HCl, the molecular weight of which is almost 500.

According to an exemplary embodiment of the present disclosure, there is now provided an iontophoretic, non-invasive transdermal delivery system for the controlled release of an ionic, pharmaceutically active ingredient (or combination of ingredients) through the skin surface of a mammal, wherein the system comprises:

a. first and second electrodes in contact with an aqueous solution comprising the ingredient in ionic and nonionic form;

b. the first electrode comprises a conductive porous polyaniline membrane, wherein the membrane is in contact with the skin surface of a mammal; and c. voltage generating means connecting said first and second electrodes, said means being capable of providing a direct current flow between the electrodes and the aqueous ingredient solution, whereby the ingredient is caused to pass through the porous membrane and is released in ionic form through the skin surface.

Another exemplary embodiment of the present disclosure is a transdermal delivery system wherein the membrane comprises polyaniline which has been doped in an acidic solution, e.g., 1N HCl for 24 hours.

Another exemplary embodiment of the present disclosure is a transdermal delivery system wherein the membrane is or functions as the anode.

Another exemplary embodiment of the present disclosure is a transdermal delivery system wherein the ingredient molecular weight is approximately equal to or less than 500.

Another exemplary embodiment of the present disclosure is a transdermal delivery system wherein the ingredient comprises doxycycline HCl, lidocaine HCl, or caffeine.

Another exemplary embodiment of the present disclosure is a transdermal delivery system wherein the ingredient comprises doxycycline HCl in an ethanol and water mixture, optionally including linoleic acid as a skin solubility enhancer.

Another exemplary embodiment of the present disclosure is a method of administering to a mammal in need thereof a therapeutically effective amount of a pharmaceutically active ingredient to treat an undesirable condition comprising:
1. providing an iontophoretic, non-invasive transdermal delivery system for the controlled release of an ionic pharmaceutically active ingredient through the skin surface of a mammal, wherein the system comprises:
   a. first and second electrodes in contact with an aqueous solution comprising the ingredient in ionic and non-ionic form;
   b. the first electrode comprises a conductive porous polyaniline membrane, wherein the membrane is in contact with the skin surface of a mammal; and
   c. voltage generating means communicating with the first and second electrodes, the voltage generating means being capable of providing a direct current flow between the electrodes and the aqueous ingredient solution, whereby the ingredient is caused to pass through the porous membrane and is released in ionic form through the skin surface;
2. contacting the skin surface of the mammal with the first electrode membrane; and
3. applying the voltage from the voltage generating means sufficient to cause the ingredient to pass through the porous membrane and be released in ionic form through the skin surface.

Another exemplary embodiment of the present disclosure is a method wherein the membrane comprises polyaniline which has been doped in an acidic solution, e.g., 1N HCl for 24 hours.

Another exemplary embodiment of the present disclosure is a method wherein the membrane is or functions as the anode.

Another exemplary embodiment of the present disclosure is a method wherein the ingredient molecular weight is approximately equal to or less than 500.

Another exemplary embodiment of the present disclosure is a method wherein the ingredient comprises doxycycline HCl, lidocaine HCl, or caffeine.

Another exemplary embodiment of the present disclosure is a method wherein the ingredient comprises doxycycline HCl in an ethanol and water mixture, optionally including linoleic acid as a skin solubility enhancer.

Additional advantageous features, functionalities and applications of the disclosed systems and methods will be apparent from the detailed description which follows, particularly when read in conjunction with the appended figures and tables.

BRIEF DESCRIPTION OF THE FIGURES

To assist one skilled in the art of making and using TDD systems of the type described herein, reference is made to the figures appended hereto.

FIG. 1 shows the iontophoretic setup using PANi film as an electrode, the anode;

FIG. 2 shows the drug reservoir with PANi and skin membranes;

FIG. 3 shows the release profiles of lidocaine HCl through mouse skin with and without a PANi membrane (i=0.2 mA/cm$^2$);

FIG. 4 shows the iontophoretic release profiles of doxycycline HCl through mouse skin with and without PANi membrane (i=0.3 mA/cm$^2$);

FIG. 5 shows SEM picture of doped PANi film used in the Ag/AgCl set for doxycycline HCl diffusion;

FIG. 6 shows SEM picture of doped PANi film used in the Ag/AgCl set for lidocaine HCl diffusion; and FIG. 7 shows SEM picture of doped PANi film used in the PANi/AgCl set for doxycycline HCl diffusion.

DETAILED DESCRIPTION OF EXEMPLARY EMBODIMENTS

In conventional iontophoresis with Ag|AgCl electrodes, the Ag electrode is the anode; the AgCl electrode acts as the cathode. The Ag electrode is easily oxidized and is therefore known to be unstable; the Ag|AgCl system is also quite costly. To overcome such limitations, a novel porous conducting polymeric membrane made of polyaniline (PANi) has been investigated here as an electrode replacing the Ag electrode in iontophoresis. As in the case of an Ag anode, the electrochemical reaction (1) at the PANi anode with an AgCl cathode is:

$$\text{PANi} + n\text{Cl}^- \rightarrow \text{PAN(Cl)}_n + ne^- \tag{1}$$

Such a system will replace the easily oxidized unstable Ag part of the traditional Ag|AgCl electrodes; at the same time a patch based on such a new system is reusable unlike the Ag|AgCl electrode since the drug agents can be refilled in the reservoir. Such a system is likely to be considerably cheaper than that based on Ag|AgCl electrodes.

As a conducting polymer, polyaniline (PANi) has been extensively investigated [11]-[14] to explore its unique properties. In the area of controlled release, its possibility to transform itself from almost an insulator to a high conductor in different pH environments has been the focus. Although many investigators have concentrated on the permeability of PANi membranes for gases, water and small carboxylic acids [11], little is available on iontophoretic TDD study, especially for large MW molecules such as lidocaine HCl, doxycycline HCl.

In the patent literature on TDD, there exists claims for the use of polyaniline as an electrode to bind agent ions (develop a reservoir) before administration and then release them when an electrical pulse or a DC voltage is applied [15-17]. A conductive membrane polymerized from materials such as polyaniline and other polymers from the polypyrrole family was proposed to split the donor chamber into two to prevent unnecessary competition of ion migration [18-20]. The PANi material was also claimed to be useful as an anode in several patents [21-23]. However, none of them disclosed a doped porous PANi membrane functioning simultaneously as an anode and a control membrane for iontophoretic drug delivery system separating the donor reservoir from the receptor as shown in FIG. 1. The proposed configuration of the two electrodes vis-à-vis the skin is however traditionally employed in iontophoresis as opposed to the electrode-network transdermal delivery system proposed by Fischer et al. [24].

The PANi membrane can control the drug release rate via its pore size and porosity and therefore provide different resistances; adjusting the voltage could lead to different current densities. Since different sizes of molecules from small (<200 D) to large (several thousand and larger) could go through such a membrane, one can deliver several agents at different rates in one system.

Therefore, according to the present disclosure, the porous conducting polymer PANi membrane film is used directly as an electrode in the iontophoretic technique, making it both a controlled release membrane and an electron carrier. Such a system advantageously eliminates the unstable Ag part of traditional Ag/AgCl electrodes; at the same time, a patch based on such a new system is reusable instead of replacing the Ag/AgCl electrode, which has heretofore been necessary according to the prior art. Not only the current density but also the membrane would control the release rate of drug: applying different pore sizes of such films and adjusting the current, different sizes of molecules from small (less than 200 D) to large (several thousand and larger) could go through, which makes it possible to deliver several agents at different rates in one TDD system according to the present disclosure. Also, such a system is likely to be considerably cheaper than a TDD system using Ag/AgCl electrodes.

Although the invention has been described with respect to the exemplary embodiments thereof, specifically using porous conductive PANi membranes as an electrode, other porous conductive polymers could be used, such as polypyrroles. Generally, such porous conductive polymers useful within the framework of the invention herein will have an average porosity in the range of from about 0.005 to about 0.6; a pore size in the range from about 10 angstrom units to about 10 microns; and must be hydrophilic.

Porous PANi membranes were prepared and used in a specific iontophoretic TDD system (FIG. 1) to study the permeation of the following agents: caffeine, lidocaine hydrochloride and doxycycline hydrochloride. FIG. 2 illustrates the details of the drug reservoir with the PANi and the mouse skin membranes. It is known that mouse skin is more permeable than human skin; our earlier studies [9] indicate that the rate of doxycycline HCl delivery achieved with mouse skin was significantly higher than that through a cadaver skin. In this work, the results obtained using this model membrane electrode have also been compared with those from regular Ag|AgCl electrodes; theoretical justification of the observed differences will also be provided. Finally, controlled release of the agents via aqueous-organic partitioning between the reservoir and the aqueous liquid in the membrane pores was also tested.

Materials and Methods
Chemicals

Polyaniline (emeraldine base, MW ca. 65,000), lidocaine hydrochloride (HCl)(MW: 270.8) were purchased from Aldrich, Milwaukee, Wis. Potassium phosphate monobasic anhydrous and linoleic acid were obtained from Sigma, St. Louis, Mo. Silver wire (99.9%, 0.5 mm), silver chloride (99.9%), hydrochloric acid solution (1M), N-methylpyrrolidinone (NMP), glycerol, light mineral oil, ethanol, methanol (HPLC-grade), acetonitrile (HPLC-grade), and doxycycline hydrochloride (HCl) (Bioreagent grade) (MW: 480.1), caffeine (MW: 194.2) were purchased from Fisher Scientific, Fair Lawn, N.J. Phosphate buffered saline (PBS) was supplied by Fluka, Milwaukee, Wis. All chemicals, except noted afterwards, were of reagent grades.

Membranes

Polyaniline membrane was cast from a concentrated solution of polyaniline (emeraldine base) (PANi) in NMP obtained by evaporation (described later).

Skin membranes: Male hairless mice, strain SKH1, 8 weeks old, were supplied by Charles River Laboratories (Wilmington, Mass.). Mice were euthanized by carbon dioxide asphyxiation. Their skins were excised and kept at −30° C. until used.

Polyvinylidene fluoride (PVDF) Durapore® hydrophilized films were purchased from Millipore Corp. (Bedford, Mass.). The polymer PVDF is naturally hydrophobic; an additional polymerized layer on the membrane surface and pores makes it hydrophilic. The geometrical characteristics of the membrane are listed in Table 1M [9, 45].

TABLE 1M

Characteristic properties of polymeric PVDF membrane

| Microporous Membrane | Material | Pore size (µm) | Porosity$^a$ | Tortuosity | Membrane thickness (µm) |
|---|---|---|---|---|---|
| PVDF film | Polyvinylidene fluoride | 0.1 | 0.7 | 2.58$^b$ | 100 |

$^a$Supplied by manufacturer.
$^b$Chen et al. [45].

Experimental Setup

Direct current (DC) was generated by the stimulus isolator purchased from World Precision Instrument, Inc., Sarasota, Fla. Standard Franz diffusion cell (Permegear, Inc., Bethlehem, Pa.) with a diffusional area of 0.64 cm$^2$ and a receptor compartment volume of 5.1 ml were used in all experiments.

EXPERIMENTAL PROCEDURE

Drug Solution

Solutions of caffeine and doxycycline HCl in water were prepared by dissolving about 200 mg of each agent into 10 ml water, while about 400 mg of lidocaine HCl was dissolved into 10 ml water. A solution of about 200 mg doxycycline HCl dissolved into an ethanol-water mixture (EtOH:H2O=2:1, v/v) with 5% v/v linoleic acid was also prepared. For the aqueous-organic partitioning system, an amount of 500 mg of doxycycline HCl was added into 50 ml light mineral oil to make a suspension [9]. No drug/agent was introduced into the PANi membrane or its solution in NMP.

Membrane Preparation and its Properties

An amount of 1.5 g of polyaniline was dissolved into 100 ml NMP and stirred for 1 hr [25]. A regular gauze pad was used to filter the resulting dark blue solution. The clear filtrate solution was then transferred to a Rotavapor® RE 111 (Flawil, Switzerland) to evaporate the solvent at 50° C. [25] for about 70 minutes to yield about 20 ml of a sticky solution. The PANi film was cast from such a solution on a glass plate. Doping such a film was achieved by keeping the film in a solution of 1N HCl for 24 hr [25], then washing it by DI water and drying it.

The porosity of the membrane, $\epsilon_m$, was obtained by measuring the weights of membrane wetted with glycerol and dry membrane, converting the difference into the void volume by taking the density of glycerol into account and then dividing by the dry volume of the film. The equation for the calculation of membrane porosity ($\epsilon_m$) is:

$$\varepsilon_m = \frac{(W_{wet} - W_{dry})/\rho_{glycerol}}{V} \quad (2)$$

where, $W_{wet}$ and $W_{dry}$ are the weights of wet and dry membrane respectively. Here $\rho_{glycerol}$ (1.475 gm/ml) and V are the density of glycerol and the volume of the membrane respectively.

The calculation of the value of the membrane parameter ($\epsilon_m/\tau_m$), where $\tau_m$ is membrane tortuosity, was carried out by measuring the flux data from three diffusion experiments of caffeine with three concentrations while all other conditions were kept the same (see Calculation A below.).

Calculation A. Calculation of the Membrane Parameter ($\epsilon_m/\tau_m$) of PANi films Combining Eqs. (4) and (5), hereinafter provided below, the equation of flux (J) is changed to:

$$J = \frac{D_{water} \cdot \varepsilon_m}{\tau_m \cdot l}(C_{1D} - C_{1R}) \quad (A\text{-}1)$$

Therefore, the membrane parameter ($\epsilon_m/\tau_m$) can be expressed as:

$$\frac{\varepsilon_m}{\tau_m} = J \cdot \frac{l}{D_{water}} \cdot \frac{1}{(C_{1D} - C_{1R})} \quad (A\text{-}2)$$

Next, three caffeine solutions of different concentrations were prepared: 5, 10, 20.4 mg/ml. From each solution in donor part, a flux value was obtained and used in Eq. (A-2) to calculate the membrane's ($\epsilon_m/\tau_m$); the averaged value, 0.0009, was used in later calculations.

In addition to the thickness (1) as a known value, the diffusion coefficient of caffeine in free solution ($D_{Caf,water}$) was obtained from the Wilke and Chang Equation [29]:

$$D_{Caf,water} = 7.4 \times 10^{-8} \frac{(\phi M_{Water})^{0.5} T}{\eta_{Water} V_{Caffeine}^{0.6}} \quad (A\text{-}3)$$

in which $M_{Water}$, $\eta_{Water}$, $V_{Caffeine}$, $\phi$ and T are the molecular weight, viscosity of water(cP), molar volume of caffeine ($cm^3$/g-mol), association factor of solvent and temperature (Kelvin) respectively. The association factor of water and molar volume are equal to 2.6, 159.3 $cm^3$/g-mol respectively, and the value of $D_{Caf,water}$ is $7.08 \times 10^{-6}$ $cm^2$/s.

Table A1 lists the membrane parameter ($\epsilon_m/\tau_m$) calculated from different flux levels for different donor concentrations; the averaged value was used in the following calculations.

TABLE A1

The value of PANi membrane parameter ($\epsilon_m/\tau_m$) calculated from data of different fluxes for caffeine*

| Concentration of caffeine (mg/ml) | Flux ($\mu g/cm^2$ h) | $\epsilon_m/\tau_m$ | Avg. $\epsilon_m/\tau_m$ |
|---|---|---|---|
| 5 | 66.6 | 0.00094 | 9E-4 ± 7E-5 |
| 10 | 136.2 | 0.00096 | |
| 20.4 | 239.5 | 0.00083 | |

*Using Eq. A-2.

In the case of skin membranes, the plastic bags containing the mouse skins were first taken out of the freezer and put into a beaker filled with room temperature water until they were defrosted. The skin samples were then removed from the plastic bags and cleaned of adhering fat deposits. They were then cut into small pieces of appropriate size and carefully mounted on top of the diffusion cells and left to equilibrate for 1 hour.

In Vitro Drug-Release Studies

The porous PANi membranes were cut to the dimensions of the Franz diffusion cells. In the case of iontophoresis-facilitated delivery, such films were applied in a large enough size to have their edges extruding out (as shown in FIG. 1) so that the film could be connected to the DC power source. The details of the preparation of Ag|AgCl electrodes, the setup of Franz diffusion cells, and sampling have been provided elsewhere [3, 9]. All results are based on an average from measurements in three Franz cells.

HPLC Analysis

For caffeine and lidocaine HCl, analysis was performed using an Agilent 1100 HPLC with a reverse-phase C18 column (Microsorb-MV™, 15 cm, 5 µm, Agilent Technologies) at a flow rate of 1 ml/min. Caffeine was detected at 270 nm with a mobile phase composed of acetonitrile: methanol: water (10:20:70) and injection volume of 20 µl. Lidocaine HCl was detected at 220 nm with a mobile phase composed of acetonitrile: 0.05 M monobasic potassium phosphate (45:55, pH 3.0) and injection volume of 40 µl. The HPLC method for doxycycline HCl has been described elsewhere [9].

SEM Imaging

The membrane structure was characterized using a scanning electron microscope (SEM) (LEO 1530 VP FE-SEM, Carl Zeiss, New York, USA).

Data Processing

The permeation parameters of the agents were calculated by plotting the cumulative corrected amounts ($\mu g/cm^2$) of the agent permeated through the skin versus time (hr). The slope of the linear portion of the graph provided the average flux value (J) at steady state ($\mu g/cm^2$-hr). The quantities $Q_8$, $Q_{10}$ and $Q_{24}$ are the accumulations respectively for 8, 10 and 24 hours in the receptor chamber.

Permeability (P) was calculated by $$P = \frac{\Delta C_{receptor}}{\Delta t \times A_{receptor}} \times \frac{V_{receptor}}{C_{donor}} \text{(cm/hr)} \quad (3)$$

Here $\Delta C_{receptor}$ (µg/ml): the difference of agent concentration in the receptor part in the given time $\Delta t$ (hr); $C_{donor}$ (µg/ml): agent concentration in the donor part; A ($cm^2$): the area of receptor; V ($cm^3$) is the receptor volume. Statistical analysis was performed using one-way analysis of variance (one way ANOVA).

Results and Discussion

The results of characterization of PANi film needed for characterizing the membrane transport of various agents through the PANi films are presented first. The release profiles through a PANi membrane of three solutes, e.g., caffeine, lidocaine HCl and doxycycline HCl are then illustrated without any iontophoresis. Next the release rates are determined from Fick's law of diffusion and compared with the experimental data. The data obtained when a mouse skin is added to the PANi film are analyzed subsequently. This has been followed by iontophoretic study of the composite of a PANi film and a mouse skin using two different kinds of electrodes, one based on a conventional Ag|AgCl electrodes and the other based on PANi|AgCl electrodes. An aqueous-organic partitioning system with doxycycline HCl as the agent present in light mineral oil as a solution-suspension was also studied at the end and the observed rates were compared with those through a porous PVDF membrane obtained earlier [9].

Properties of PANi Films

The porosity of PANi films was found to be 0.67%±0.08% based on the measurements from three films. The value of the porosity is quite low. Introduction of low levels of pore forming agents in the casting solution would have led to higher porosity. It is known from standard techniques employed to make porous membranes by phase inversion techniques that the surface porosity of ultrafiltration membranes are in the range of 0.5-2% [26]. Thus the low porosity of the PANi membrane is not unusual. The value of the membrane parameter ($\epsilon_m/\tau_m$) including membrane porosity and tortuosity was found to be 9E-4±7E-5 from an average of nine films (see Calculation A). The thickness of the PANi films was found to be 0.018 mm±0.002 mm.

Release Profiles from PANi Membranes

The release rates of three agents through the PANi membrane as obtained in the Franz cell are presented in Table 1.

between the reservoir liquid (aqueous solution) and membrane pore liquid (aqueous solution) is assumed to be 1.

The effective diffusion coefficient of the agent through water in the porous membrane may be defined as [28]

$$D_{eff} = \frac{D_{water}\varepsilon_m}{\tau_m} \quad (5)$$

Wilke-Chang equation [29] was used to estimate the free diffusion coefficient in solution, $D_{water}$, of different agents. Since the concentrations in the receptor part were always much less than those in the donor part and the receptor side was well mixed, $C_{1R}$ was assumed to be 0 for the following calculations. The implications of ionization on the partitioning behavior were also considered in such calculations [9]. As for doxycycline HCl, since the donor solution concentration was higher than 0.01M, its dimerized form was included in the calculation of its model flux value as well [30]. Therefore, the flux in the model calculations has contributions from three components: flux of the base ($J_{Doxy}$), flux of the ionized base

TABLE 1

Permeation data of three agents released through PANi membrane and comparison of predicted flux data with experimental values.

| Agent | Permeability (cm/hr) | Flux (µg/cm² hr) | $D_{water-agent}$ (cm²/s) | Model prediction of flux (µg/cm² hr) | $Q_{24}$* (µg/cm²) |
|---|---|---|---|---|---|
| Caffeine | 1.2E−2 ± 9.0E−3 | 240 ± 177 | 7.08E−6 | 260 | 573 ± 246 |
| Lidocaine HCl | 1.1E−2 ± 3.5E−3 | 461 ± 147 | 7.91E−6 | 573 | 3330 ± 1760 |
| Doxycycline HCl | 3.5E−3 ± 7.0E−4 | 72 ± 14 | 6.59E−6 | 198 | 307 ± 97 |

*24 hours accumulation in the receptor part.

This table illustrates the permeation data for three different agents in terms of their permeability, flux and 24-hr accumulation values. Obviously, doxycycline HCl, with the highest MW, had the lowest flux, permeability and accumulation. Between caffeine and lidocaine HCl, although their diffusion coefficients are quite close, the higher concentration of lidocaine HCl in the aqueous donor solution (by a factor of two) played a critical role in providing almost two-fold higher flux and six fold higher drug accumulation compared to those for caffeine. The following calculations provide a possible explanation of the data.

Conventionally, the value of the flux of the permeating species may be obtained by simple diffusion through the water-filled membrane pores [27]:

$$J = D_{eff}\frac{\Delta C}{l} = \frac{D_{eff}}{l}(C_{1D} - C_{1R}) \quad (4)$$

in which, $D_{eff}$ is the effective diffusion coefficient in the membrane, $\Delta C$ is the concentration difference in the pore liquid of the two external solution-pore liquid interfaces on two sides of the membrane: $C_{1D}$ is the concentration in the pore liquid on the donor side and $C_{1R}$ is that in the receptor side; l is the membrane thickness. The last formula is utilized in the following calculation with $C_{1R} \cong 0$, effectively zero concentration in the receiver vessel having an aqueous phase; for the donor chamber, $C_{1D} \cong C$, which is the agent concentration in the donor solution. The partition coefficient K of the agent ($J_{DoxyH+}$) and flux of the dimer ($J_{dimer}$). As for lidocaine HCl, however, such data for its dimerization are not available in literature; therefore, a general calculation was carried out using methods disclosed in reference [9]. Results of model flux values (J) obtained when all experimental parameters were introduced into Eq. (4), are also shown in Table 1, which includes the corresponding experimentally observed values. Detailed calculation methodologies and results are provided in Calculation B below.

Calculation B. Calculation of Model Flux for Table 1

1. Model Flux of Caffeine

Since caffeine is a neutral molecule which does not produce any charged ions in solution, its flux is determined simply by using its concentration values in Eq. (4), where the donor solution concentration of caffeine is 20400 µg/ml, $$J = \frac{D_{eff}}{l}(C_{1D} - C_{1R})$$

$$= \frac{7.08 \times 10^{-6}}{0.0018} \times 0.0009 \times (204000 - 0) \times 3600$$

$$= 260.0 \text{ µg/cm}^2\text{h}$$

2. Model Flux of Doxycycline HCl

Reference [9] describes generally how to calculate the model flux value of an ionizable salt agent. Since the concentration of doxycycline HCl was quite high (0.0425 M), the role of its dimerization has to be considered in the flux calculation [30].

There are four species of doxycycline agent in the aqueous phase; the formula of each and the symbol for its concentration are indicated in separate brackets: the original base doxycycline (Doxy) ($C_{Doxy}$), doxycycline H$^+$ (DoxyH$^+$) ($C_{DoxyH^+}$), doxycycline dimer (DoxyH$^+$)$_2$ ($C_{di}$) or (Doxy)$_2$H$^+$ ($C_{di}$) [30].

First, the total concentration $C_T$ of doxycycline in all forms was related to the total concentration ($C_m$) of Doxy ($C_{Doxy}$) and DoxyH$^+$ ($C_{DoxyH^+}$) as the monomer forms of doxycycline by the following equation from Reference [30]:

$$C_T = C_m + 2K_d C_m^2 \quad (B\text{-}1)$$

where $K_d$ is the dimerization constant and equal to 24 [30], while $$C_T = C_m + C_{di} = 20400 \; \mu g/ml = 0.0425 \; mol/l \quad (B\text{-}2)$$

where $C_{di}$ is the concentration of doxycycline dimer.

By solving Eq. (B-1) for this value of $C_T$, $$C_m = C_{Doxy} + C_{DoxyH^+} = 0.0211 M \quad (B\text{-}3)$$

$$C_{di} = 0.0214 M = 10274 \; \mu g/ml \quad (B\text{-}4)$$

From Eq. (B-3), the concentration values of each monomer form of doxycycline were obtained by the solution of a quadratic equation obtained from Eq. (B-5) [9]:

$$K_1 = 10^{-3.3} = \frac{[Doxy] \cdot [H^+]}{[DoxyH^+]} \quad (B\text{-}5)$$

By solving Eq. (B-5) together with Eq. (B-3), $C_{Doxy} = 3.01 \times 10^{-3} M = 1445 \; \mu g/ml$, and $C_{DoxyH^+} = 0.0181 M = 8685 \; \mu g/ml$.

Using Wilke-Chang estimation method [29], the diffusion coefficients of monomers and dimers of doxycycline HCl in free solution are (see [9] for $D_{DoxyH^+,water}$ and the same method for that of dimers):

$$\begin{cases} D_{Doxy,water} = 3.93 \times 10^{-6} \; cm^2/s \\ D_{DoxyH^+,water} = 6.59 \times 10^{-6} \; cm^2/s \\ D_{(DoxyH^+)_2,water} = D_{(Doxy)_2H^+,water} = 4.58 \times 10^{-6} \; cm^2/s \end{cases} \quad (B\text{-}6)$$

Therefore, the total flux of doxycycline HCl had three components: $J_{Doxy}$, $J_{DoxyH^+}$ and $J_{dimer}$:

$$\begin{aligned} J &= J_{Doxy} + J_{DoxyH^+} + J_{dimer} \quad (B\text{-}7) \\ &= (3.93 \times 10^{-6} \times 1445 + 6.59 \times 10^{-6} \times 8685 + 4.58 \times 10^{-6} \times 10274) \times \\ &\quad 0.50 \times 3600 \\ &= 197.9 \; \mu g/cm^2 h \end{aligned}$$

where $\left(\frac{\varepsilon_m}{\tau_m}\right) \cdot \frac{1}{l} = 0.50 \; cm^{-1}$.

Without consideration of the existence of dimer forms of doxycycline HCl, the predicted value of flux would be 232.0 $\mu g/cm^2 h$.

3. Model Flux of Lidocaine HCl

Similarly, the model flux of lidocaine HCl should have three parts also. But the formation of its dimers under high concentration as 0.1485 M is so far a hypothesis [42]; the following calculation is therefore based on the general method followed in Reference [9].

There are two species of lidocaine agent in the aqueous phase, the undissociated lidocaine (Lido) and lidocaine H$^+$ (LidoH$^+$). There are two unknowns here whose values are needed before the total agent flux can be calculated. First, the relative distribution between the two species has to be determined. Second, their diffusion coefficients also need to be known. The first dissociation equilibrium constant $K_1$ for lidocaine H$^+$ is $10^{-7.2}$ [43]:

$$K_1 = 10^{-7.2} = \frac{[Lido] \cdot [H^+]}{[LidoH^+]} \quad (B\text{-}8)$$

For a total agent concentration of lidocaine HCl, $$C_T = C_{Lido} + C_{LidoH^+} = 40220 \; \mu g/ml = 0.1485 \; mol/l \quad (B\text{-}9)$$

the following values were obtained for the individual species by the solution of a quadratic equation obtained from Eq. (B-8): $C_{Lido} = 26 \; \mu g/ml$ and $C_{LidoH^+} = 40194 \; \mu g/ml$. It was assumed that their concentration in the receptor was zero. Therefore the total agent flux is:

$$J = \frac{D_{Lido}}{l} \cdot \left(\frac{\varepsilon_m}{\tau_m}\right) \cdot (C_{Lido} - 0) + \frac{D_{LidoH^+}}{l} \cdot \left(\frac{\varepsilon_m}{\tau_m}\right) \cdot (C_{LidoH^+} - 0) \quad (B\text{-}10)$$

The diffusion coefficients of lidocaine in free solution ($D_{Lido,water}$) can be obtained from the Wilke-Chang Equation and is equal to $4.91 \times 10^{-6} \; cm^2/sec$. The diffusion coefficient of $D_{LidoH^+}$ compound is to be obtained from considerations of diffusion potential-based diffusion coefficient $D_{LidoH^+Cl^-}$ obtained from the individual values of $D_{LidoH^+}$ and $D_{Cl^-}$ and their charges:

$$D_{LidoH^+Cl^-} = \frac{D_{LidoH^+} \cdot D_{Cl^-} (z_+ - z_-)}{(z_+ \cdot D_{LidoH^+} - z_- \cdot D_{Cl^-})} \quad (B\text{-}11)$$

$D_{LidoH^+}$ for this calculation is assumed essentially equal to $4.91 \times 10^{-6} \; cm^2/sec$ corresponding to the undissociated $D_{Lido}$. Here $z_+ = +1$, $z_- = -1$ and $D_{Cl^-} = 2.03 \times 10^{-5} \; cm^2/sec$ [44], so that $$\begin{aligned} D_{LidoH^+Cl^-} &= \frac{4.91 \times 10^{-6} \times 2.03 \times 10^{-5} [1 - (-1)]}{4.91 \times 10^{-6} - (-2.03 \times 10^{-5})} \\ &= 7.91 \times 10^{-6} \; cm^2/sec \end{aligned}$$

Therefore, the total flux of lidocaine HCl in both forms from Eq. (B-10) is:

$$\begin{aligned} J &= (4.91 \times 10^{-6} \times 26 + 7.91 \times 10^{-6} \times 40194) \times 0.50 \times 3600 \\ &= 572.5 \; \mu g/cm^2 h \end{aligned}$$

If dimerization existed and its effect were included in the calculation, the model flux would be lower as shown in the calculation for doxycycline HCl.

The experimental obtained flux values shown in Table 1 appear to be not far from those calculated from the model equations especially for caffeine and lidocaine HCl. If existence of dimerization of lidocaine HCl were considered, the model value would probably have been closer to the experimental one. All differences are likely to be due to the variations from film to film cut from different parts of a larger piece of film. From these results, it is clear that such a slightly porous polymeric conducting membrane is unlikely to be a major obstacle for these agents to pass through. Therefore, a mouse skin was used next for tests with a PANi membrane placed on top of it.

Release Profiles from a Composite of PANi and Mouse Skin Membranes

The release flux values of three agents through a composite membrane consisting of a porous PANi membrane with a mouse skin next to it were 7.6±0.6, 20.4±1.0, 0 µg/cm²-hr for caffeine, lidocaine HCl and doxycycline HCl respectively. It appears that doxycycline HCl, the largest molecule, had apparently no release at all. Compared with the data from earlier experiments [9], it is not surprising; without an appropriate enhancer in the donor solution, it is very difficult for doxycycline HCl to go through the mouse skin. For caffeine and lidocaine HCl, the magnitude of the higher concentration of lidocaine HCl solution is believed to have played a greater role here. Iontophoresis was therefore employed next as an enhancement.

As discussed in a previous work [9], mouse skin was used in this study since it was an initial feasibility investigation. It is known to the authors, however, that data from mouse skin provide higher permeability values than would be observed in human cadaver skin.

Iontophoretic Release Profiles from PANi Membranes

For caffeine and lidocaine HCl, the current density used was 0.2 mA/cm² because of their relatively small MWs; for doxycycline HCl, 0.3 mA/cm² was chosen because its MW is 480.1. To study the iontophoretic property of the PANi membranes, standard Ag|AgCl electrode was used. The values of the release flux rates of the three agents were 305±79, 411±144, 793±111 µg/cm²-hr for caffeine, lidocaine HCl and doxycycline HCl respectively. As for caffeine, a neutral molecule, there was about 30% increase in its flux (vis-á-vis Table 1), which has been mainly brought about by electroosmosis [31-33]. For doxycycline HCl, the flux increased more than ten times (see Table 1), which indicated potentially a promising release behavior if applied on top of a mouse skin. A skin patch can deliver about 0.8 mg of doxycycline HCl in, say, one hour through a contact area of 1 cm². For lidocaine HCl, however, there is a small decrease in the flux.

According to Faraday's law, the iontophoretic flux of an ion can be expressed as [34, 35]

$$J_i = \frac{t_i i}{F Z_i} \quad (6)$$

in which, i, F, $t_i$, and $Z_i$ are respectively the applied current density, Faraday's constant, the transport number of ionic species i and the electrochemical valence of the ion i under consideration. To simplify the calculation of $t_i$, when the donor part contains only the agent solution without any other ion, the major competing ion with the agent ion is Cl⁻, whose $t_{Cl^-}$ may be assumed to be 0.86 [36]. The transport number for the agent ion is then most likely to be 0.14. As for lidocaine HCl, similarly, its cation transport number can be tentatively assumed as 0.19 [37]. For the values of the current density applied, and the electrochemical valence for the agent ion, the calculated flux results for lidocaine HCl and doxycycline HCl are shown in Table 2; they have also been compared with the experimentally observed values. For both lidocaine HCl and doxycycline HCl, the experimental values are quite close to the calculated values.

TABLE 2

Comparison of model predictions with experimental iontophoretic flux data

| Agent ion | Current density (mA/cm²) | Valence $Z_i$ | Model prediction of flux* (µg/cm² hr) | Experimental flux (µg/cm² hr) |
|---|---|---|---|---|
| Lidocaine HCl Ion | 0.2 | 1 | 383 | 411 ± 144 |
| Doxycycline HCl ion | 0.3 | 1 | 752 | 793 ± 111 |

*Calculated from equation (6).

Iontophoretic Release Profiles from Both PANi and Mouse Skin Membranes

Three sets of iontophoretic experiments were carried out. In the first set, as a control test, traditional Ag|AgCl electrodes were used for the mouse skin only without the PANi membrane. In the other two sets, with the PANi membrane and the mouse skin together, either PANi|AgCl configuration or the Ag|AgCl configuration as electrodes was tested.

Lidocaine HCl

The results of the three sets of experiments are presented in FIG. 3. Table 3 illustrates the permeation data for the different experimental configurations.

TABLE 3

Iontophoretic permeation data of lidocaine HCl released through mouse skin with and without a PANi membrane (i = 0.2 mA/cm²)

| Set | Permeability (cm/hr) | Flux (µg/cm² hr) | $Q_{10}$* (µg/cm²) |
|---|---|---|---|
| Skin only Ag|AgCl electrodes | 1.1E-2 ± 2.6E-4 | 433 ± 10 | 4160 ± 138 |
| PANi + skin Ag|AgCl electrodes | 1.0E-3 ± 4.2E-4 | 48 ± 20 | 348 ± 78 |
| PANi + skin PANi|AgCl electrodes | 1.0E-3 ± 3.5E-4 | 43 ± 15 | 392 ± 130 |

*10 hours accumulation in the receptor part.

The results of the two different sets of electrodes were similar, which indicates that the conducting PANi membrane could be a good replacement for the Ag electrode. In addition, if its properties such as porosity is increased (correspondingly tortuosity is likely to be reduced), it is possible for a given applied voltage to enhance the flux and accumulation of drug released, i.e., an additional way to control transdermal drug delivery.

Doxycycline HCl

It should be noted that for the sets of PANi membrane and mouse skin together, no release was achieved in the absence of a chemical enhancer added to the aqueous donor agent solution (as observed in reference [9] for conventional porous uncharged polymeric membranes). Therefore, instead of using a simple aqueous solution, 5% linoleic acid was added to the doxycycline HCl solution consisting of ethanol and water (EtOH: water=2:1, v/v). The reason for using ethanol was to increase the solubility of linoleic acid in the water.

Conventionally ethanol is used as a chemical enhancer in many TDD applications. [38, 39] However, our earlier investigation [9] of TDD of doxycycline HCl indicated that ethanol as well as many other common chemical enhancers, such as Azone™, cineole etc. were not able to enhance the transport of the large polar molecule, doxycycline HCl. However, linoleic acid at 5-10% level was quite successful in enhancing the transport of doxycycline HCl substantially. Thus here both chemical enhancement and physical enhancement are active in pushing doxycycline HCl through.

The results of three sets of experiments are presented in FIG. 4. Table 4 illustrates the permeation data for doxycycline HCl under different conditions.

TABLE 4

Iontophoretic permeation data of doxycycline HCl released through mouse skin with and without a PANi membrane ($i = 0.3$ mA/cm$^2$)

| Set | Permeability (cm/hr) | Flux (μg/cm$^2$ hr) | $Q_{24}$ (μg/cm$^2$) |
|---|---|---|---|
| Skin only Ag\|AgCl electrodes | 3.8E−3 ± 6.7E−4 | 48.5 ± 8.5 | 1020 ± 642 |
| PANi + skin Ag\|AgCl electrodes | 0 | 0 | 0 |
| PANi + skin PANi\|AgCl electrodes | 5.6E−3 ± 4.8E−3 | 94.4 ± 81.2 | 2760 ± 3980 |

Unlike the data obtained with lidocaine HCl, no release of doxycycline HCl was observed from the Ag|AgCl electrode set. By the end of the experiment, a white gel-like layer of AgCl was observed on the surface of the PANi film facing the Ag electrode (FIG. 5). It is possible that the deposited matter blocked the pathway for doxycycline HCl through the membrane first, and hence no drug was detected passing through the skin. Compared with the lidocaine HCl, it is believed that with the increased ethanol in the agent solution needed to solubilize the linoleic acid, we also created conditions for increased dissolution of AgCl [40, 41]. However, as shown in the SEM picture (FIG. 5), such an increased solubility of AgCl as a complex led to its precipitation on the PANi membrane surface. Since the solubility of AgCl in the lidocaine case was much smaller in the absence of alcohol, small individual particles were observed on the PANi film facing the Ag electrode (FIG. 6). For the PANi|AgCl electrodes set, however, since Ag was not used as electrode, no AgCl blocked the release (FIG. 7) and the results were even better than those of skin only set due to the enhancements of both iontophoresis and linoleic acid. The high values of deviations could be from the non-homogeneous porous structure of the mounted membranes, which is more important for larger molecules like doxycycline HCl than smaller ones like lidocaine HCl.

Aqueous-Organic Partitioning System

For the permeation study of PANi membrane based on aqueous-organic partitioning system, doxycycline HCl suspension in light mineral oil was used as the donor solution so that its permeation results would be compared with those from a hydrophilized polyvinylidene fluoride (PVDF) membrane in a general way. Table 5 illustrates the permeation data of doxycycline HCl through a PANi membrane based on aqueous-organic partitioning system with those through a hydrophilized PVDF membrane [9] for comparison.

TABLE 5

Permeation data of doxycycline HCl through PANi membrane based on aqueous-organic partitioning system with those through PVDF system

| Membrane system | Permeability (cm/hr) | Flux (μg/cm$^2$ hr) | Q (μg/cm$^2$) |
|---|---|---|---|
| PANi | 0.003 ± 0.002 | 31 ± 18 | 6 hr: 80 ± 46 |
| PVDF | 0.03 ± 0.01 | 146 ± 27 | 24 hr: 1440 ± 240 |

Compared to permeation data from the PVDF membrane system, all flux values obtained here are much smaller. It is believed that the rather small porosity (for PANi, about 1%; for PVDF, 70%) is the primary reason for this low delivery rate. Therefore it would be essential to increase the PANi membrane porosity to further improve delivery from both aqueous solution system and aqueous-organic partitioning system. However, PANi membrane is anyway not a good candidate for non-iontophoresis systems [9]. On the other hand, it has been clearly shown earlier that it is quite good for iontophoretic TDD.

CONCLUSIONS

Iontophoretic TDD was studied using porous membranes of polyaniline, a conducting polymer. Three model agents of different molecular weights, caffeine, lidocaine HCl and doxycycline HCl, were studied. The transport rate of each agent through such a conducting membrane was predicted well using simplified mass transport models. Satisfactory release profiles were achieved not only from the in vitro membrane test but also from in vitro iontophoretic TDD system using mouse skin. Iontophoresis with PANi|AgCl electrodes presented satisfactory release data indicating a potential for practical use. As a dosage of 100 mg/day is required for prophylaxis, a small patch of five-centimeter diameter will work. For aqueous-organic partitioning systems, due to the rather low porosity of PANi membrane, the permeation rates were much lower than those from their hydrophilized PVDF counterpart membranes. It is understood that porous membranes made from conducting polymers, other than polyaniline, are also contemplated within the scope of the disclosed invention herein.

REFERENCES

1. W. E. Rhodes III, Iontophoretic drug delivery: new advantages revitalize an established technology, Drug Delivery Technology, 2 (6) (2002), 34-37.
2. R. Panchagnula, P. O. Pillai, V. B. Nair and P. Ramarao, Iontophoresis revisited, Current Opinion in Chemical Biology, 4 (2000) 468-473.
3. Y. Wang, Q. Fan, Y. Song, B. Michniak, Effects of fatty acids and iontophoresis on the delivery of midodrine hydrochloride and the structure of human skin, Pharm. Res. 20 (2003) 1612-1618.
4. Y. N. Kalia, A. Naik, J. Garrison, R. H. Guy, Iontophoretic drug delivery, Adv. Drug Del. Rev. 56 (2004) 619-658.
5. S. Farrell, A Controlled Release Technique Using Microporous Membranes, Ph. D. Dissertation, New Jersey Institute of Technology, 1996.
6. S. Farrell, K. K. Sirkar, A reservoir-type controlled release device using aqueous-organic partitioning and a porous membrane, J. Membr. Sci. 130 (1997) 265-274.
7. S. Farrell, K. K. Sirkar, A mathematical model of an aqueous-organic partition-based controlled release system using microporous membranes, J. Controlled Rel. 61 (1999) 345-360.
8. S. Farrell, K. K. Sirkar, Mathematical model of a hybrid dispersed network-membrane-based controlled release system, J. Controlled Rel. 70 (2001) 51-61.
9. Q. Fan, K. K. Sirkar, Y. Wang, B. Michniak, In vitro delivery of doxycycline hydrochloride based on a porous membrane-based aqueous-organic partitioning system, J. Controlled Release, 98 (3) (2004) 355-365.

10. Recommendations for the Prevention of Malaria Among Travelers, Morbidity and Mortality Weekly Report, 39 (RR-3) (1990) 1-10.
11. L. Wen, N. M. Kocherginsky, Doping-dependent ion selectivity of polyaniline membranes, Syn. Metals, 106 (1999) 19-27.
12. P. Wang, K. L. Tan, E. T. Kang, K. G. Neoh, Preparation and characterization of semi-conductive poly(vinylidene fluoride)/polyaniline blends and membranes, Applied Surfaces Sciences, 193 (2002) 36-45.
13. G. Illing, K. Hellgardt, R. J. Wakeman, A. Jungbauer, Preparation and characterization of polyaniline based membrane for gas separation, J. Membrane Sci., 184 (2001) 69-78.
14. Mirmohseni, R. Solhjo, Preparation and characterization of aqueous polyaniline battery using a modified polyaniline electrodes, Euro. Polym. J., 39 (2003) 219-223.
15. J. R. Reynolds, H. Ly, J. Kinlen, Burst electrode, U.S. Patent Application Pub. No.: 2002/0022826 A1, Feb. 21, 2002.
16. R. P. Haak, F. Theeuwes, J. R. Gyory, Electrotransport transdermal system, U.S. Pat. No. 4,927,408, May 22, 1990.
17. E. J. Parsi, Cell for electrically controlled transdermal drug delivery U.S. Pat. No. 4,731,049, Mar. 15, 1988.
18. J. B. Phipps, Iontophoresis electrode, U.S. Pat. No. 5,057,072, Oct. 15, 1991.
19. J. B. Phipps, Iontophoresis electrode, U.S. Pat. No. 5,084,008, Jan. 28, 1992.
20. J. E. Sanderson, S. R. Deriel, Method and apparatus for Iontophoretic drug delivery, U.S. Pat. No. 4,722,726, Feb. 2, 1988.
21. J. Siman, J. Dove, Medical devices having improved antimicrobial/antithrombogenic properties, U.S. Pat. No. 6,273,875 B1, Aug. 14, 2001.
22. E. R. Scott, Electrotransport device electrode assembly having lower initial resistance, U.S. Pat. No. 6,195,582 B1, Feb. 27, 2001.
23. D. F. Untereker, J. B. Phipps, G. A. Lattin, Iontophoretic drug delivery, U.S. Pat. No. 5,135,477, Aug. 4, 1992.
24. W. Fischer, R. Haas, C. Zimmermann, Transdermal delivery system (TDS) with electrode network, U.S. Patent Application Pub. No.: 2004/0193089 A1, Sep. 30, 2004.
25. G. MacDiarmid, E. Scherr, X. Tang, High molecular weight polyaniline films, U.S. Pat. No. 5,484,884, 1996.
26. M. Cheryan, Ultrafiltration and Microfiltration Handbook, CRC Press, Boca Raton, Fla., 1998.
27. S. B. Kessler, E. Klein, in W. S. Winston Ho, K. K. Sirkar (Ed.), Membrane Handbook, Chapman and Hall, New York, 1992, Chapter 11; Kluwer Academic, Boston (2001).
28. R. Prasad, K. K. Sirkar, Dispersion-free solvent extraction with microporous hollow-fiber modules, AIChE. J. 44 (1988) 177-188.
29. C. R. Wilke, P. Chang, Correlation of diffusion coefficients in dilute solutions, AIChE J. 1 (1955) 264-270.
30. J. B. Bogardus, R. K. Blackwood, Jr., Solubility of doxycycline in aqueous solution, J. Pharm. Sci. 68 (1979) 188-194.
31. M. J. Pikal, The role of electroosmotic flow in transdermal iontophoresis, Advanced Drug Delivery Reviews, 9 (2-3) (1992) 201-237.
32. P. Singh, H. I. Maibach, Iontophoresis in drug delivery: basic principles and applications, Critical Reviews in Therapeutic Drug Carrier Systems, 11 (2&3) (1994) 161-213.
33. J. E. Riviere, M. C. Heit, Electrically-assisted transdermal drug delivery, Pharm. Research, 14 (6) (1997) 687-697.
34. J. B. Phipps, R. V. Padmanabhan, G. A. Lattin, Iontophoretic delivery of model inorganic and drug ions, J. of Pharm. Sci. 78(5) (1989) 365-369.
35. K. Banga, Electrically Assisted Transdermal and Topical Drug Delivery, Taylor & Francis Inc., London, UK, 1998, Chapter 2.
36. D. Marro, Y. N. Kalia, M. B. Delgado-Charro, R. H. Guy, Optimizing iontophoretic drug delivery: identification and distribution of the charge-carrying species, Pharm. Res. 18 (12) (2001) 1709-1713.
37. K. Karami, H. SjÖberg, P. Beronius, Ionization conditions for iontophoretic drug delivery. Electrical conductance and aggregation of lidocaine hydrochloride in 1-octanol at 25° C., Int. J. Pharm. 154 (1997) 79-87.
38. K. A. Walters, in J. Hadgraft, R. H. Guy (Ed.), Transdermal Drug Delivery, Developmental issues and research initiatives, Marcel Dekker, Inc., New York, 1989, Chapter 10.
39. C. Williams, B. W. Barry, Penetration enhancers, Adv. Drug Del. Rev., 56 (2004) 603-618.
40. J. Kratohvil, B. Tezak, The influence of the composition and the properties of the solvent on complex formation between silver and chloride, bromide, iodide, and thiocyanate ions, Recueil des Travaux Chimiques des Pays-Bas et de la Belgique, 75 (1956) 774-780.
41. K. P. Anderson, E. A. Butler, D. R. Anderson, E. M. Woolley, The solubility of silver chloride and the concentration of silver-containing species in ethanol-water mixtures, J. Physical Chemistry, 71 (11) (1967) 3566-3569.
42. Personal communication with Dr. Per Beronius, Sep. 13, 2004.
43. H. SjÖberg, K. Karami, P. Beronius, L. SundelÖf, Ionization conditions for iontophoretic drug delivery. A revised pKa of lidocaine hydrochloride in aqueous solution at 25° C. established by precision conductometry, Int. J. Pharm. 141 (1996) 63-70.
44. J. S. Newman, Electrochemical Systems, Prentice-Hall, Englewood Cliffs, N.J., pp. 227, Table 75-1, 1973.
45. H. Chen, A. S. Kovvali, S. Majumdar, K. K. Sirkar, Selective CO2 separation from CO2-N2 mixtures by immobilized carbonate-glycerol membranes, Industrial and Engineering Chemistry Research 38(9) (1999) 3489-3498.

What is claimed is:

1. An iontophoretic, non-invasive transdermal delivery system for the controlled release of a pharmaceutically active ingredient through the skin surface of a mammal, wherein the system comprises:

a. first and second electrodes in contact with an aqueous solution comprising the pharmaceutically active ingredient, wherein said first electrode is a conductive porous polyaniline membrane that is adapted to be placed in contact with the skin surface of a mammal; and b. voltage generating means connecting said first and second electrodes, said means being capable of providing a direct current flow between the electrodes and the aqueous ingredient solution, whereby the pharmaceutically active ingredient is caused to pass through the conductive porous polyaniline membrane and the skin surface; and wherein the porous polyaniline membrane is configured and dimensioned to allow non-ionic materials to pass through the pores of the porous polyaniline membrane;

wherein the conductive porous polyaniline membrane has an average porosity from about 0.005 to about 0.60; and wherein the pores of the porous polyaniline membrane have pore sizes from about 10 angstrom units to about 10 microns.

2. The system of claim 1 wherein the conductive porous polyaniline membrane comprises polyaniline which has been doped in a solution of 1N HCl for 24 hours.

3. The system of claim 2 wherein the conductive porous polyaniline membrane is the anode.

4. The system of claim 3 wherein the pharmaceutically active ingredient molecular weight is less than 500.

5. The system of claim 4 wherein the pharmaceutically active ingredient comprises doxycycline HCl, lidocaine HCl or caffeine.

6. The system of claim 5 wherein the pharmaceutically active ingredient comprises doxycycline HCl in an ethanol and water mixture.

7. A method of administering to a mammal in need thereof a therapeutically effective amount of a pharmaceutically active ingredient to treat an undesirable condition comprising;
   providing an iontophoretic, non-invasive transdermal delivery system for the controlled release of a pharmaceutically active ingredient through the skin surface of a mammal, wherein the system comprises:
   a. first and second electrodes in contact with an aqueous solution comprising the pharmaceutically active ingredient, wherein the first electrode is a conductive porous polyaniline membrane that is in contact with the skin surface of a mammal; and
   b. voltage generating means connecting said first and second electrodes, said means being capable of providing a direct current flow between the electrodes and the aqueous ingredient solution, whereby the pharmaceutically active ingredient is caused to pass through the conductive porous polyaniline membrane and through the skin surface;
   contacting the skin surface of the mammal with the first electrode membrane; and
   applying the voltage from the voltage generating means sufficient to cause the pharmaceutically active ingredient to pass through the conductive porous polyaniline membrane and the skin surface; and
   wherein the porous polyaniline membrane is configured and dimensioned to allow non-ionic materials to pass through the pores of the porous polyaniline membrane;
   wherein the conductive porous polyaniline membrane has an average porosity from about 0.005 to about 0.60; and
   wherein the pores of the porous polyaniline membrane have pore sizes from about 10 angstrom units to about 10 microns.

8. The method of claim 7 wherein the conductive porous polyaniline membrane comprises polyaniline which has been doped in a solution of 1N HCl for 24 hours.

9. The method of claim 8 wherein the conductive porous polyaniline membrane is the anode.

10. The method of claim 9 wherein the pharmaceutically active ingredient molecular weight is less than 500.

11. The method of claim 10 wherein the pharmaceutically active ingredient comprises doxycycline HCl, lidocaine HCl or caffeine.

12. The method of claim 11 wherein the pharmaceutically active ingredient comprises doxycycline HCl in an ethanol and water mixture.

13. The system of claim 6 wherein the pharmaceutically active ingredient further comprises linoleic acid as a skin solubility enhancer.

14. The method of claim 12 wherein the pharmaceutically active ingredient further comprises linoleic acid as a skin solubility enhancer.

15. The system of claim 1 wherein the delivery of a direct current flow between the electrodes is effective to cause the pharmaceutically active ingredient to be released in ionic form through the skin surface.

16. The method of claim 7 wherein the pharmaceutically active ingredient passes through the conductive porous polyaniline membrane and is released in ionic form through the skin surface.

* * * * *